(12) United States Patent
Davies et al.

(10) Patent No.: US 8,318,525 B2
(45) Date of Patent: Nov. 27, 2012

(54) GAS SENSING DEVICE

(75) Inventors: David Frank Davies, Southampton (GB); Ian Paul Andrews, Portsmouth (GB); Anthony Richard Cowburn, Eastleigh (GB); Stuart Christopher Cutler, Hampshire (GB)

(73) Assignee: City Technology Limited, Portsmouth (GB)

( * ) Notice: Subject to any disclaimer, the term of this patent is extended or adjusted under 35 U.S.C. 154(b) by 1260 days.

(21) Appl. No.: 10/535,567

(22) PCT Filed: Nov. 25, 2003

(86) PCT No.: PCT/GB03/00512
§ 371 (c)(1), (2), (4) Date: May 19, 2005

(87) PCT Pub. No.: WO2004/048955
PCT Pub. Date: Jun. 10, 2004

(65) Prior Publication Data
US 2006/0032745 A1  Feb. 16, 2006

(30) Foreign Application Priority Data
Nov. 27, 2002 (GB) .................................. 0227686.3
Jul. 16, 2003 (GB) .................................. 0316642.8

(51) Int. Cl.
*G01N 27/16* (2006.01)

(52) U.S. Cl. ................ 438/55; 438/49; 438/54; 422/83; 422/94; 422/95; 422/96; 422/97; 73/23.2; 73/23.31; 73/25.03

(58) Field of Classification Search ............... 422/83, 422/94–67; 438/49, 54, 55; 73/23.2, 23.31, 73/25.03
See application file for complete search history.

(56) References Cited

U.S. PATENT DOCUMENTS

| | | | | |
|---|---|---|---|---|
| 3,481,179 | A | * | 12/1969 | Howarth ..................... 73/23.21 |
| 4,352,099 | A | * | 9/1982 | Christen et al. ............... 340/633 |
| 5,070,721 | A | * | 12/1991 | Tantram ..................... 73/23.31 |
| 5,601,693 | A | * | 2/1997 | Davies ......................... 204/400 |
| 5,624,641 | A | * | 4/1997 | Capetanopolous et al. ..... 422/98 |
| 5,948,988 | A | * | 9/1999 | Bodin ............................. 73/706 |
| 6,351,982 | B1 | | 3/2002 | Tindal et al. |
| 6,395,585 | B2 | | 5/2002 | Brandl ........................ 538/127 |

(Continued)

FOREIGN PATENT DOCUMENTS
DE      35 14830      10/1985
(Continued)

OTHER PUBLICATIONS

English language translation of WO 00/00820, Daeche et al., Jan. 6, 2000, p. 1-12.*

*Primary Examiner* — In Suk Bullock
*Assistant Examiner* — Robert Eom
(74) *Attorney, Agent, or Firm* — Husch Blackwell LLP

(57) ABSTRACT

A device for sensing a gas comprises a plastics housing (106, 107) moulded in situ around at least one portion of a conducting lead frame (100), the housing defining an enclosure (113) and being provided with means for enabling gas flow into the enclosure. A gas sensitive element (114) within the enclosure (113) is mounted to the conducting lead frame (100). The conducting lead frame (100) comprises connection leads which are accessible through, and at least partially encapsulated by, the wall of the housing.

7 Claims, 14 Drawing Sheets

U.S. PATENT DOCUMENTS 7,479,255 B2 * 1/2009 Otani et al. .................. 422/94

FOREIGN PATENT DOCUMENTS

| | | |
|---|---|---|
| DE | 198 28 662 | 1/2000 |
| EP | 0940680 A2 * | 4/1999 |
| EP | 1134557 | 3/2001 |
| JP | 2002-295795 * | 10/2002 |
| WO | WO 00/00820 | 1/2000 |
| WO | PCT/GB03/05126 | 11/2003 |

* cited by examiner

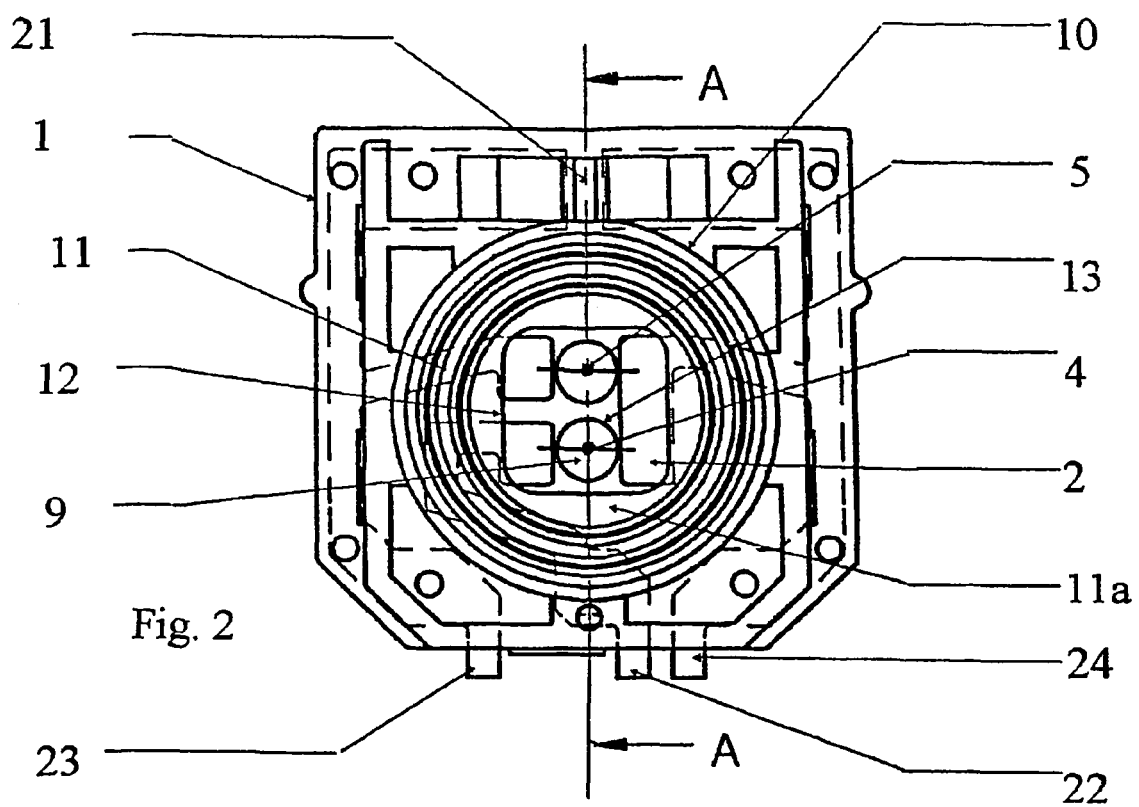

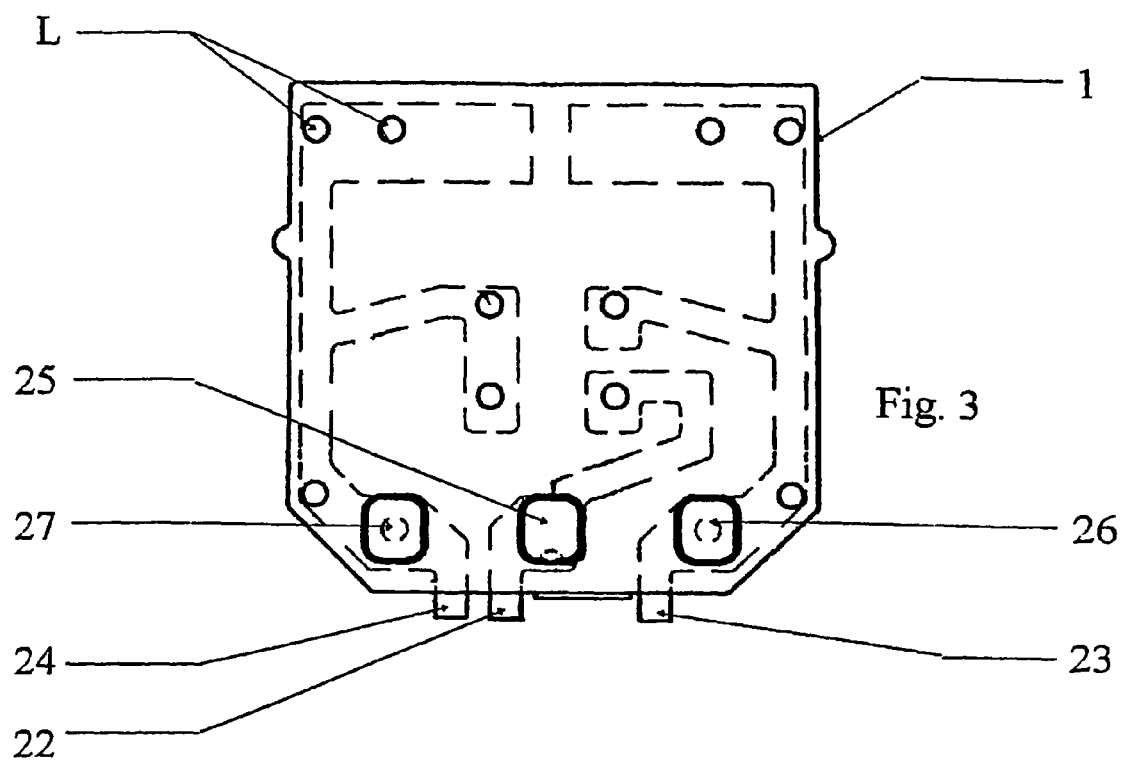

Fig. 5a
Fig. 5b
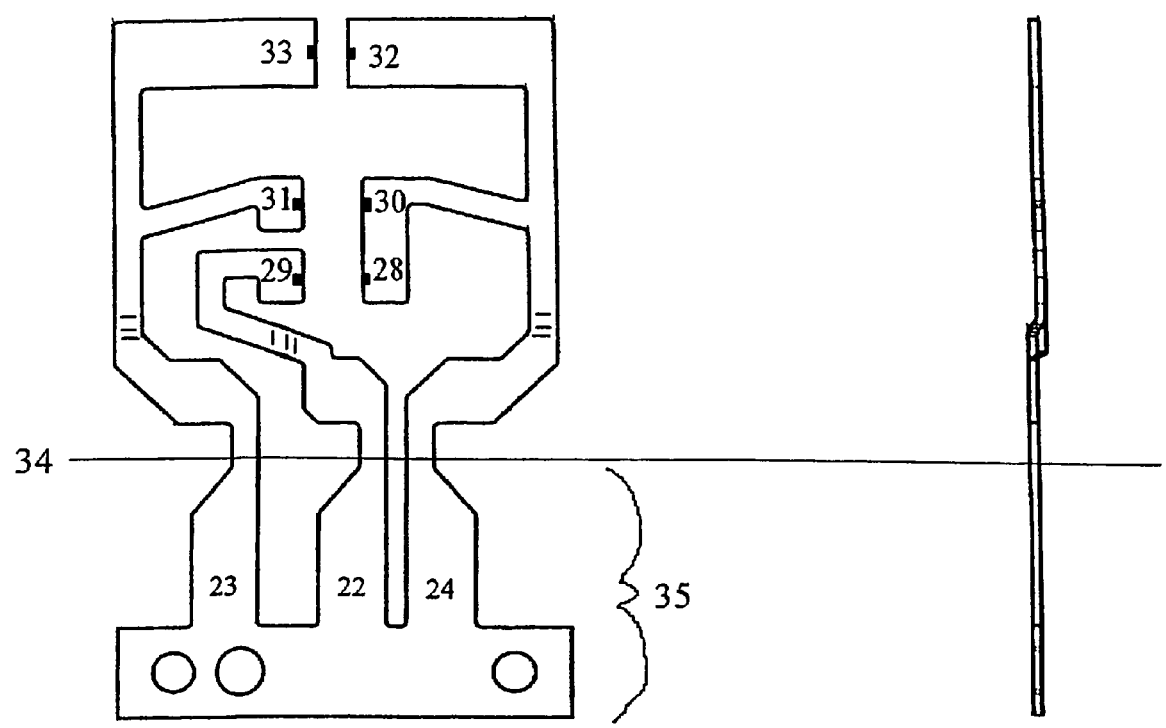

GAS SENSING DEVICE

This invention relates to a device for sensing a gas, in particular a flammable gas, in air.

Catalytic oxidation is a well established and often used method for detecting flammable gases in which an element is heated in order to oxidise any flammable gas present. During oxidation, heat is evolved which causes the temperature of the element to rise and results in an increase in its electrical resistance which may be detected to indicate the presence of a flammable gas. Typically, the element comprises a filament of thin metal wire on which a porous bead is formed which includes a catalyst. Commonly, one such element is used in conjunction with a second, of similar construction but catalytically inactive, in a Wheatstone bridge circuit. Thus the inert element may act as a control, compensating for variations in ambient temperature. To ensure combustion of the flammable gas, the elements must be operated at an elevated temperature, of the order of 500° C.

To ensure safe operation of such a device, the elements must be enclosed within a housing which prevents gas outside the device being ignited by the gas undergoing combustion inside. However, in order for the device to function, gas must be able to flow into the enclosure. This is achieved by the inclusion of a flame arrestor in the housing, such as a metal mesh or a sinter element, through which gas may enter the device yet an ignition source may not escape.

Certain regulations must be met by the housing in order for it to be certified as flameproof and capable of withstanding the rapid and significant changes which can arise on combustion of the flammable gas inside the device. These changes may be in terms of pressure, temperature, chemical composition etc. All in all, the device must not allow ignition of the external gas mixture, irrespective of the conditions inside the device. This is achieved by a number of precautions, including:

the use of a flame arrestor to conduct heat away sufficiently rapidly that a flame cannot propagate through this component;

ensuring that the strength of the housing materials and design is sufficient to prevent rupturing as a result of extreme conditions inside; and confirming that any gas expelled from the sensor has insufficient energy to cause an external ignition, for example by limiting its exit rate and temperature.

In virtually all cases, it is necessary to provide the device with components which must pass through the housing wall, for example electrical connectors. This results in gaps between the housing and the protruding component(s) which could allow ignited gas to escape. In such a situation, the device must be provided with one or more layers of potting compound, cement or other encapsulant which serve to seal the gaps and complete the flameproof enclosure. At present, there are regulations which specify the minimum thickness of such layers. In the UK, the potting compound typically has a minimum thickness of 3 mm.

The result is a final device size which is significantly larger than the volume required by the operational components alone. It would be advantageous to reduce the size of the final product, and in particular reduce it from a 3 dimensional object to a substantially flat device. This would lead to possible new uses of such a gas sensor, such as a clip-on badge sensor which could be worn by workers in a potentially dangerous industrial situation, for example.

The majority of known flameproof housings are cast from metal and require several millimeters of potting compound and flame arrestor material, as well as impact protection for the flame arrestor in order fully to meet the relevant safety and performance standards. EP-A-0667519 achieves a small reduction in device size by mounting the gas sensitive elements onto a track carrying substrate such that they may be contained within the thickness of a typical PCB. However, the remainder of the device is largely conventional and hence the final size is not significantly reduced.

GB-B-2328508 describes a method of joining the flame arrestor to the housing which overcomes the need for precision machining and accelerates the fixing operation whilst producing a join which is certifiably flameproof. The invention makes use of a plastics housing which is moulded in situ around the flame arrestor, which is in the form of a metal sinter material. This does not however address the issue of device size.

In accordance with a first aspect of the present invention a device for sensing a gas comprises at least one gas sensitive element contained within a flameproof, plastics housing supporting a flame arrestor which enables gas to flow into the interior of the housing, and the gas sensitive element(s) being connected to conducting leads which are accessible through, and are at least partially encapsulated by, the wall of the housing, the encapsulating wall having sufficient thickness such that the housing will not allow the propagation of an ignition source from within the device to the ambient atmosphere, under working conditions.

This first aspect of the invention further provides a method of manufacturing a device for sensing a gas, the method comprising moulding a plastics housing in situ directly around a set of conducting leads, mounting at least one gas sensitive element inside the housing and connecting it or them to the conducting leads which are accessible through, and at least partially encapsulated by, the wall of the housing, the encapsulating wall having sufficient thickness that the housing will not allow the propagation of an ignition source from within the device to the ambient atmosphere, under working conditions, and securing a flame arrestor to the housing which completes the flameproof enclosure yet enables gas to flow into the interior.

The present invention eliminates the requirement for a layer of potting compound. By encapsulating a sufficient length of the conducting leads in the plastic wall (by which we mean that there is intimate contact between the wall and the conducting leads), there is no gap at the metal/plastic interface which could allow ignited gas or another such ignition source to escape the flameproof enclosure. Therefore a significant size reduction is possible and a substantially flat device may be constructed. In particular, by enabling the use of electrically insulating (plastic) materials for the enclosure around the electrical connectors, a whole new range of design freedoms are made possible. Previous inventions such as GB-B-2328508 have not recognised such materials as suitable to fulfil this role. One key benefit of the present invention is the ability to arrange that encapsulation occurs in the horizontal plane rather than in a vertical direction as would usually be the case for a practical, compact, potted device.

Preferably, the plastics housing is fabricated by moulding in situ the plastics material directly around the conducting leads. This method not only produces a flameproof seal between the conducting leads and the housing but also simplifies the assembly process, being less expensive and more easily controllable than traditional methods of incorporating electrical connections through the housing wall, which involve potting. Potting requires liquid handling and pouring, and the potting material may undergo contraction during solidification which must be compensated for by making the layer thicker than would otherwise be necessary. It is therefore highly advantageous to form a flameproof seal in one moulding step, without the need for potting.

Preferably, the device further comprises at least one filter in order to remove contaminants from the gas flow into the device. Certain substances may have a detrimental effect on the operation of the device should they reach the gas sensitive elements, and should therefore be removed by appropriate filters. Generally, at least one filter is provided which removes hydrogen sulphide from the gas flow into the device. Typically, at least one of the filter(s) are inboard of the flame arrestor. This provides some degree of protection and holds them in place without the need for further fixings. However filters may also be located outboard of the flame arrestor, possibly held in place by at least one clip.

The device preferably further comprises means for protecting one or more of the gas sensitive element (s) from shock damage. This aims to minimise damage should the device suffer mechanical shock. Generally, the device further comprises means for insulating the gas sensitive element(s) and electrical connections, either in terms of electrical insulation or heat insulation, or both. Preferably, the protecting and/or insulating means comprise at least one layer of shock absorbent and insulating material. The two functions may be carried out by the same material, provided it is inert, has suitable mechanical properties and low heat conductance. Typically, the shock absorbent and/or insulating material is glass wool.

Preferably, the flame arrestor is provided by a metal mesh. This is an advantageous alternative to using a sintered metal powder, since an equivalent flameproof standard may be achieved using a thinner section. Generally, the flame arrestor is joined to the plastics housing by a process of thermal bonding around its perimeter. This is achieved by applying pressure to the periphery via a hot workpiece, and results in a flameproof bond between the flame arrestor and the housing, by means of plastic flow into the voids in the metal mesh.

Typically, the device further comprises a compensating element, which behaves similarly to the gas sensitive element except in its response to the gas. When the device is connected to detector circuitry, the two elements form part of a Wheatstone bridge circuit which provides a signal proportional to the gas concentration. Generally, the gas sensitive element comprises a catalytic bead, such as a pellistor. The compensating element is catalytically inactive. However, the gas sensitive element could also comprise a micromachined or planar pellistor or other types of heated gas sensor, for example semiconductor sensors or those which rely on thermal conductivity to detect gas.

Preferably, each gas sensitive element and/or compensating element is positioned at least partly within a recess in an interior wall of the housing. Also preferably, each recess also contains means for the protection and insulation of the gas sensitive element positioned at least partly inside it. This provides further protection against impact damage and reduces heat loss from the gas sensitive elements.

The thickness of the portion of the housing wall through which the conducting leads extend is usually substantially at least 6 mm. The length of encapsulation of the conducting leads will be chosen to meet the safety requirements for flameproof certification, which may change in due course as standards evolve.

Although the encapsulation length may be longer than with conventional potted devices, there is greatly increased design freedom. For example, typically, the flame arrestor is located above the gas sensitive element(s), the conducting leads extending out through a side wall of the housing. This has the advantage of making it possible to construct a substantially flat device.

Preferably, the conducting leads are coupled with respective contacts located in an integral extension of the housing. This configuration enables the device to be connected to other electrical components in a variety of ways, as may be chosen to suit each respective application.

Conveniently, the conducting leads are provided by a conducting lead frame fabricated prior to encapsulation by the plastics housing. By "lead frame", we refer to a conducting portion of the device, rather than to a frame made out of lead (Pb). This enables straightforward moulding of the plastics housing directly around the metal, and is more convenient than incorporating more than one component during the moulding process.

Typically, the conducting leads will form pads flush or sub flush to the housing although they could extend or protrude through the housing.

In the preferred example, the housing is formed by moulding the plastics material around the lead frame and subsequently mounting the other components. However in some situations it may be more appropriate to mould the housing around more of the components, in situ. For example, the gas sensitive element(s) could be connected to the lead frame before the housing is moulded.

Preferably, the device further comprises means for retaining components located outboard of the flame arrestor. Typically, the retaining means is provided by a bezel which fastens mechanically to the housing. The bezel also provides some degree of mechanical protection for the flame arrestor and filter(s).

In accordance with a second aspect of the invention, a device for sensing a gas comprises a plastics housing moulded in situ around at least one portion of a conducting lead frame, the housing defining an enclosure and being provided with means for enabling gas flow into the enclosure, and at least one gas sensitive element within the enclosure mounted to the conducting lead frame, wherein the conducting lead frame comprises connection leads which are accessible through, and are at least partially encapsulated by, the wall of the housing.

This second aspect of the invention further provides a method of manufacturing a device for sensing a gas, the method comprising moulding a plastics housing in situ around at least one portion of a conducting lead frame such that the housing defines an enclosure, providing the housing with means for enabling gas flow into the enclosure, mounting at least one gas sensitive element inside the enclosure and connecting it to the conducting lead frame, and providing the conducting lead frame with connection leads which are accessible through, and at least partially encapsulated by, the wall of the housing.

By overmoulding the lead frame, the housing acts not only as an enclosure and support for the sensor components and electrical connections but also as insulating means between conducting regions. This makes it possible to reduce the size of the sensor envelope and can simplify the manufacturing process by reducing the number of assembly steps required.

Generally, portions of the lead frame are left uncovered by the plastics housing. This provides suitable connection points to which electronic components may be mounted. Typically, the device further comprises an electronic component mounted onto at least some of the portions of the conducting lead frame not covered by the plastics housing. Preferably, the electronic component is a memory component, but it could also or alternatively comprise components such as analogue to digital converters, amplifiers or microprocessors mounted in a similar manner. If desired, several electronic components could be connected to the conducting lead frame, the lead frame fulfilling the function of a circuit board in creating the required interconnections. In the case of a memory component, the memory component is preferably an EEPROM although it could be many other types of memory chip. The memory component generally stores data relating to the gas sensitive element, but it could also hold any other information of value to the sensor user, such as date of manufacture, calibration data and temperature compensation coefficients.

By attaching an EEPROM or other component directly to the lead frame, it becomes an integral part of the sensor construction, rather than an add-on component housed in an extension to the sensor envelope as previously known. In this respect, the lead frame acts not only as a sensor support and means of electrically connecting power and signal inputs to and from the sensor, but also as means of electrically connecting power to the EEPROM and also transmission of signals into and out from the EEPROM. Further, the lead frame provides the basic structure of the connector used to interface the completed sensor system to external circuitry.

Conveniently, the device further comprises a cap which covers at least some of the portions of the conducting lead frame not covered by the plastics housing. Such a cap could be a separate moulding which snaps onto the sensor housing or the cap could be moulded directly onto the device during an additional moulding step. The cap provides protection for the exposed parts of the lead frame and any electronic components attached thereto.

Preferably, the lead frame is overmoulded by the plastics housing in two steps rather than one, so that the plastics housing comprises at least an inner portion and an outer portion, the outer portion being moulded around the inner portion. Alternatively, the two steps could be combined into one. However, by forming the housing in two steps, it is possible to tune the properties of the plastics materials used to suit the sensor and the application. For example, different plastics may be used to form the outer and inner parts of the housing. Also, in practice, it is difficult to mould a relatively large volume of material around the lead frame in a single step.

It is preferable that the or each gas sensitive element is a semiconductor gas sensor although other forms of sensor might be employed such as those based on conductive polymers or ion selective FET structures. If a semiconductor sensor is employed, preferably the or each semiconductor gas sensor comprises a p-type mixed metal oxide semiconducting material of the first, second and/or third order transition metal series, wherein the semiconductor gas sensor is responsive to a change in concentration of carbon monoxide in the surrounding atmosphere.

It is further envisaged that certain features of sensors according to the first aspect of the invention may be incorporated into a sensor according the second aspect of the invention, or vice versa. For instance, the overmoulded lead frame can be designed to provide a flameproof seal between the conductive frame and the housing. By providing the sensor with a flame arrestor, the enclosure may be arranged to be flameproof and the device used to detect combustible gases by means of a pellistor or other suitable gas sensitive element.

Examples of a gas sensors incorporating a device for sensing a gas in accordance with the present invention will now be described with reference to the accompanying drawings, in which:

FIG. 2 is a schematic plan view of the housing, gas sensitive elements and conducting leads as shown in FIG. 1 but with the conducting leads extending out of the housing;

FIG. 3 is an underneath plan of the device as shown in FIG. 1;

Figure 6:
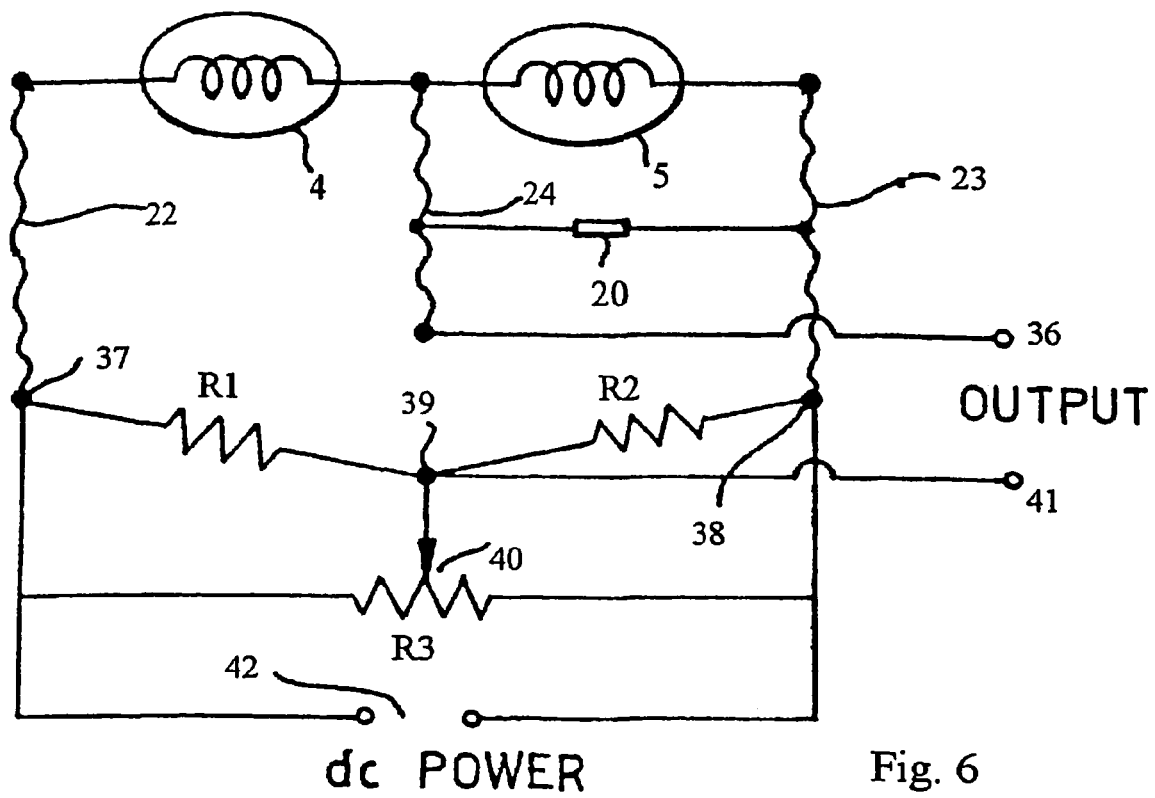
Figure 7:
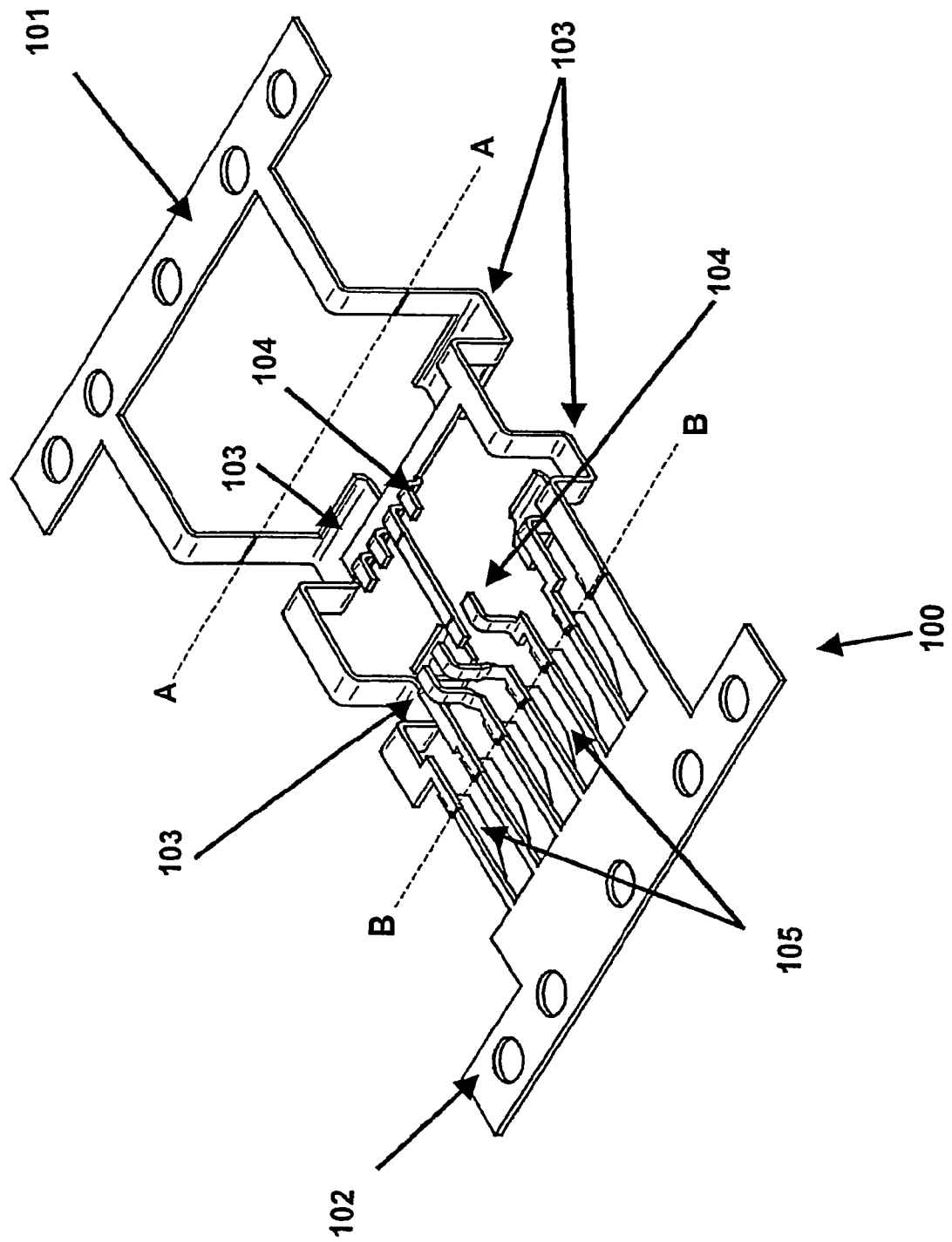
Figure 8:
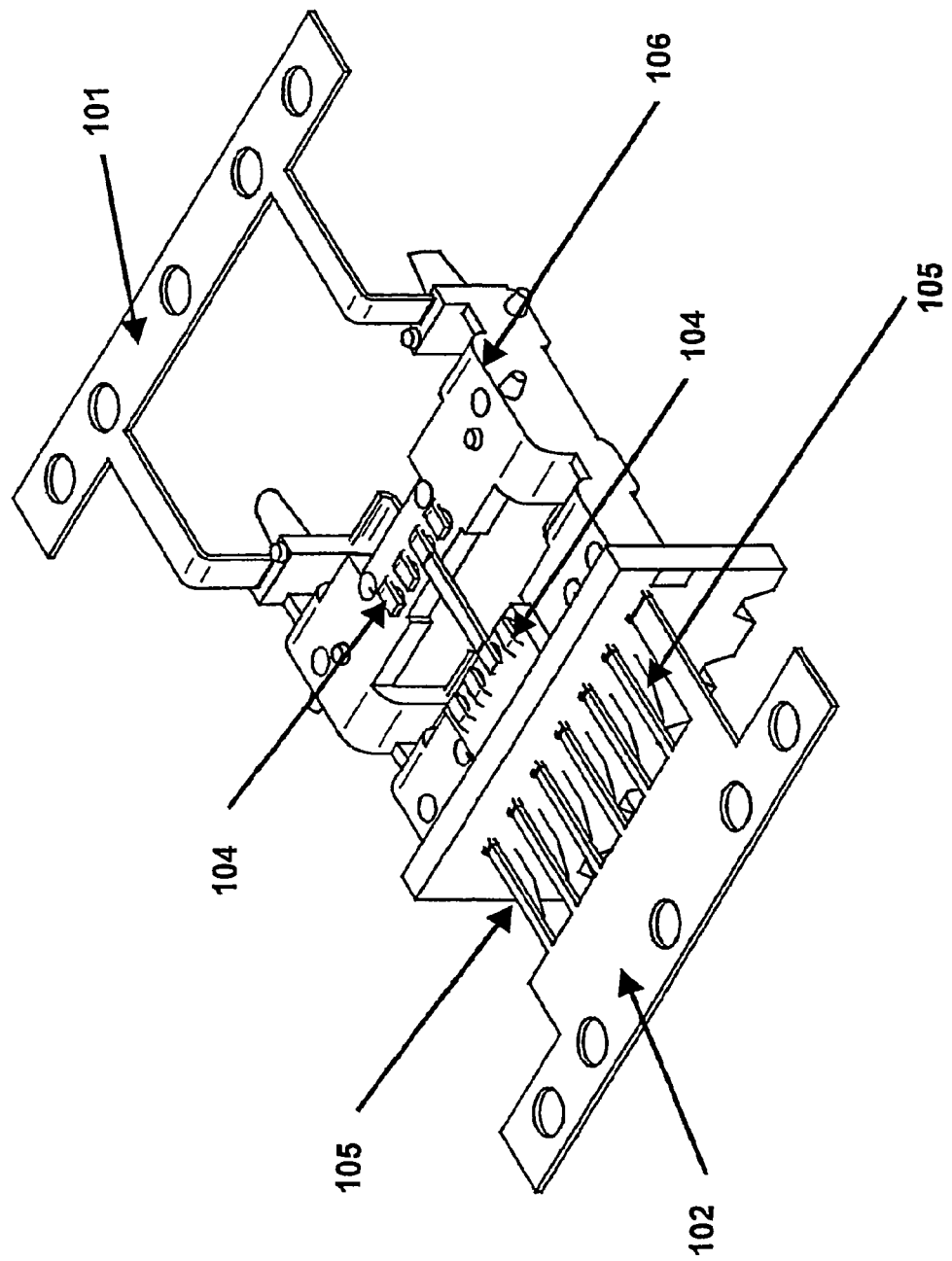
Figure 9:
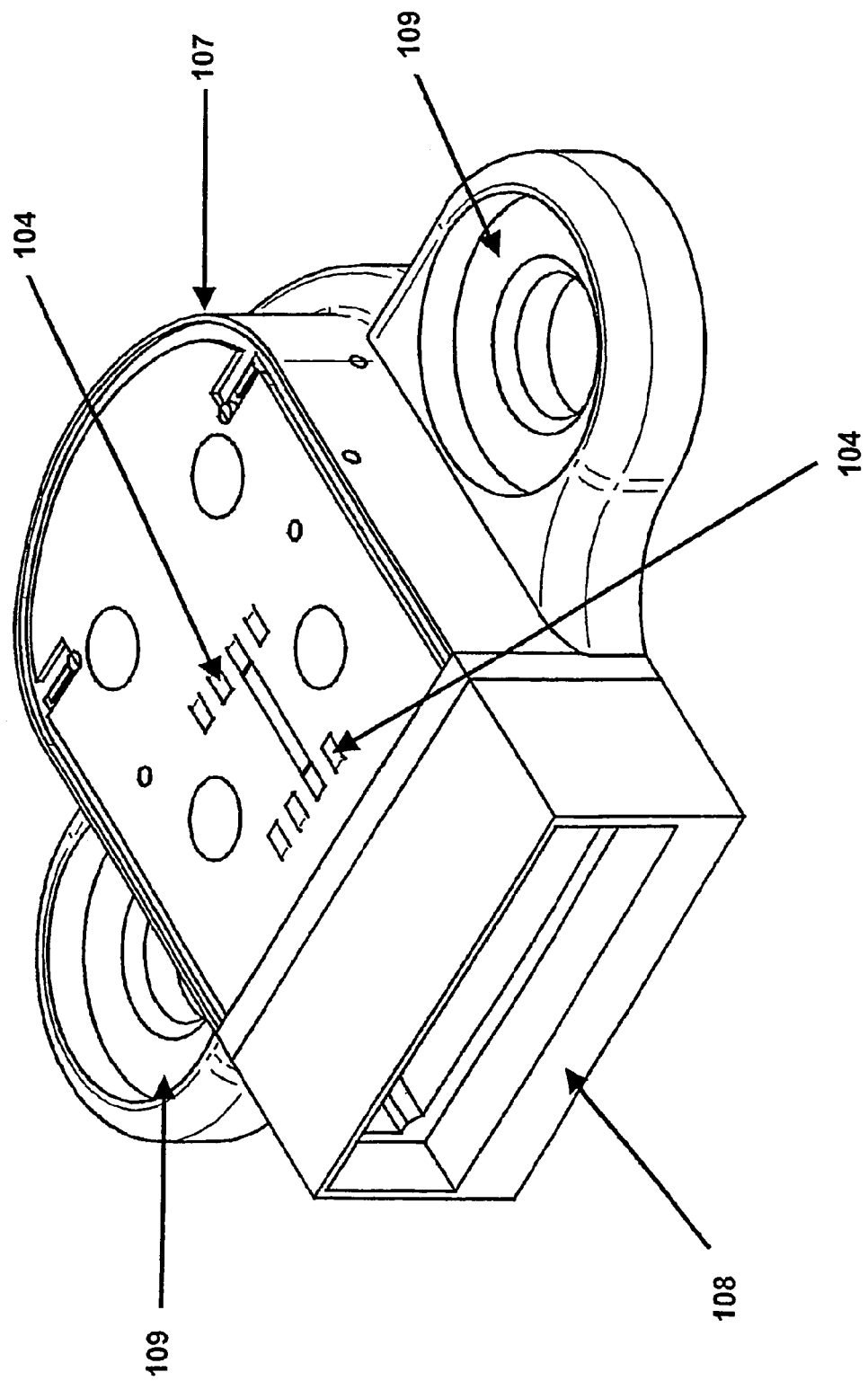
Figure 10:
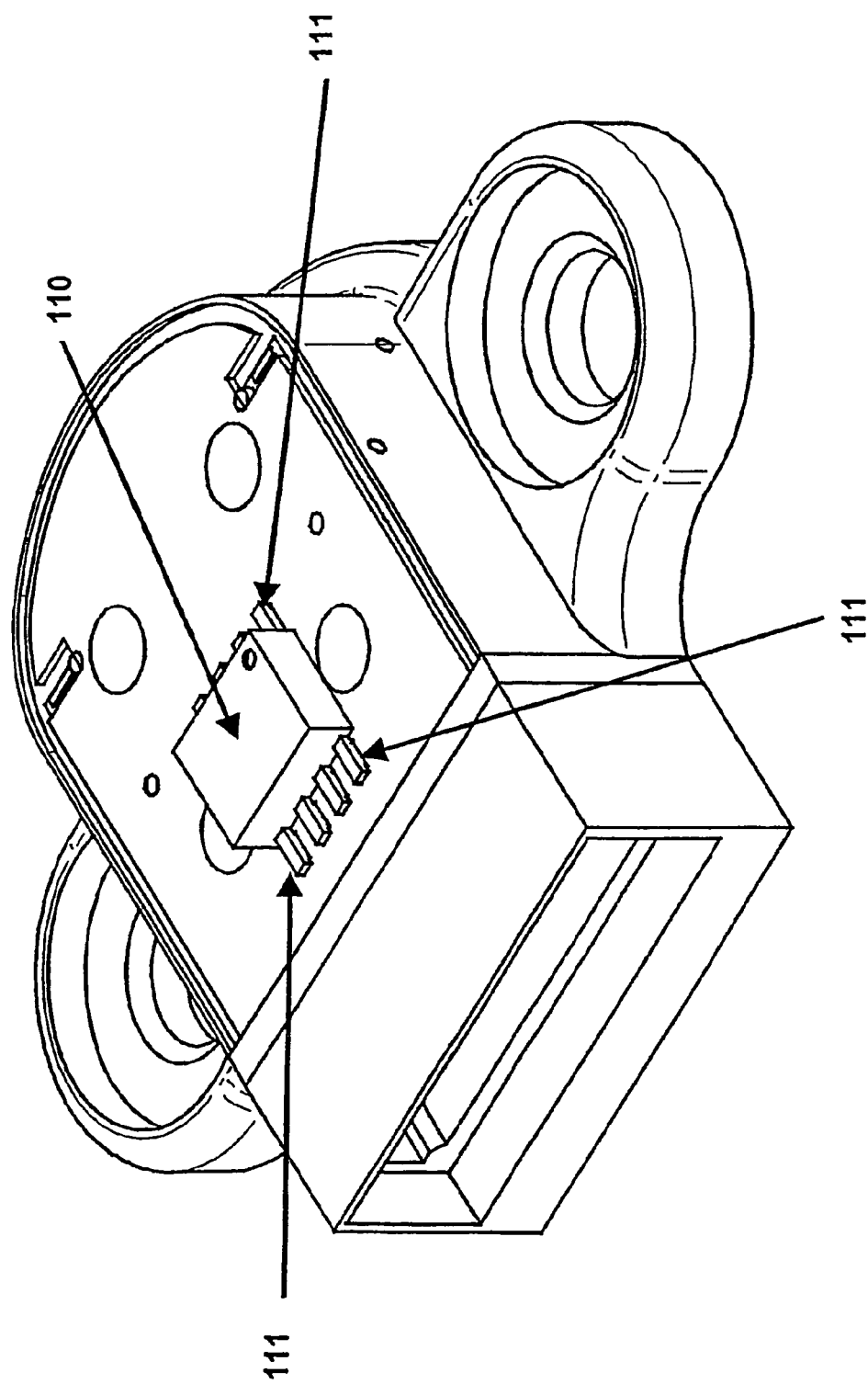
Figure 11:
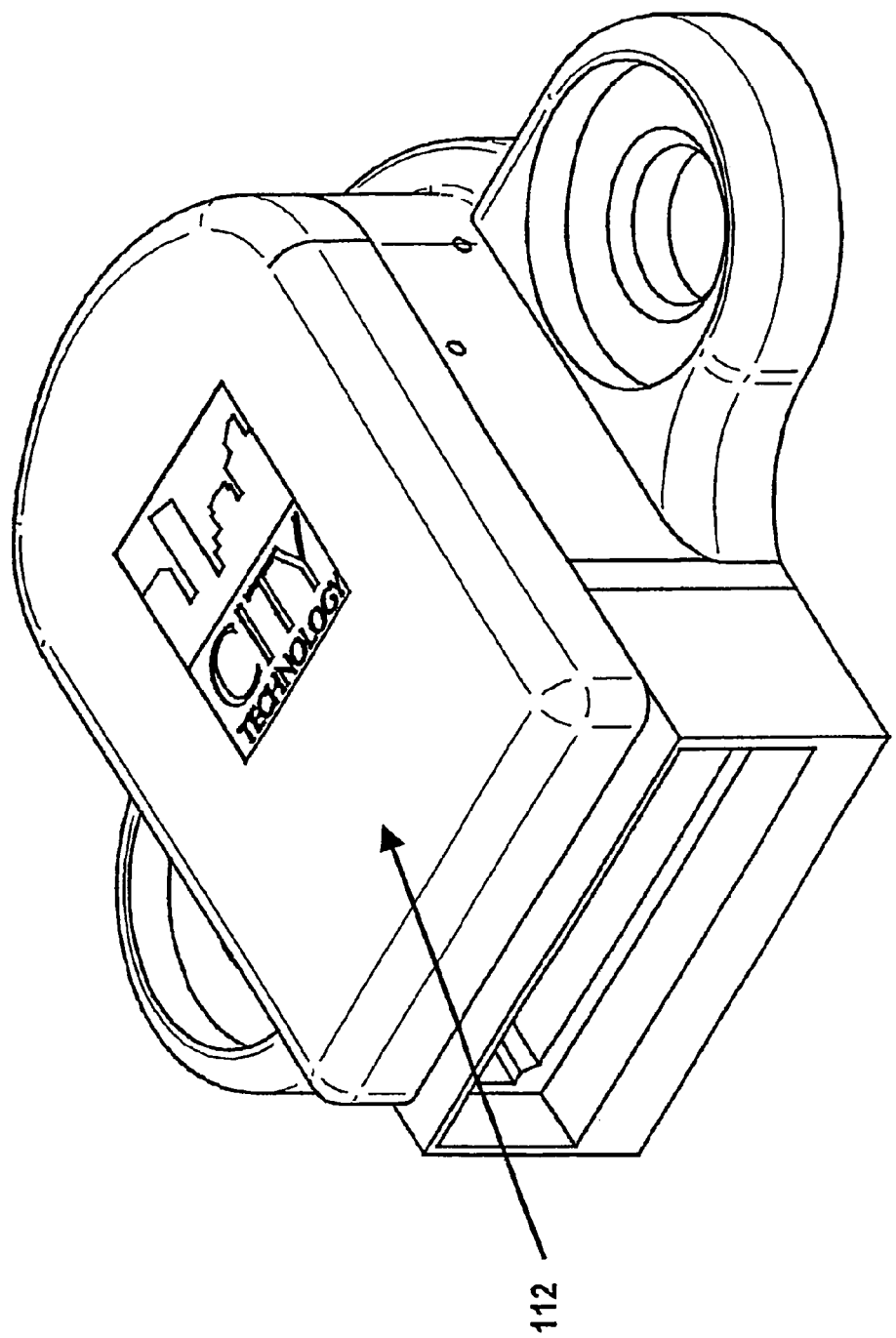
Figure 12:
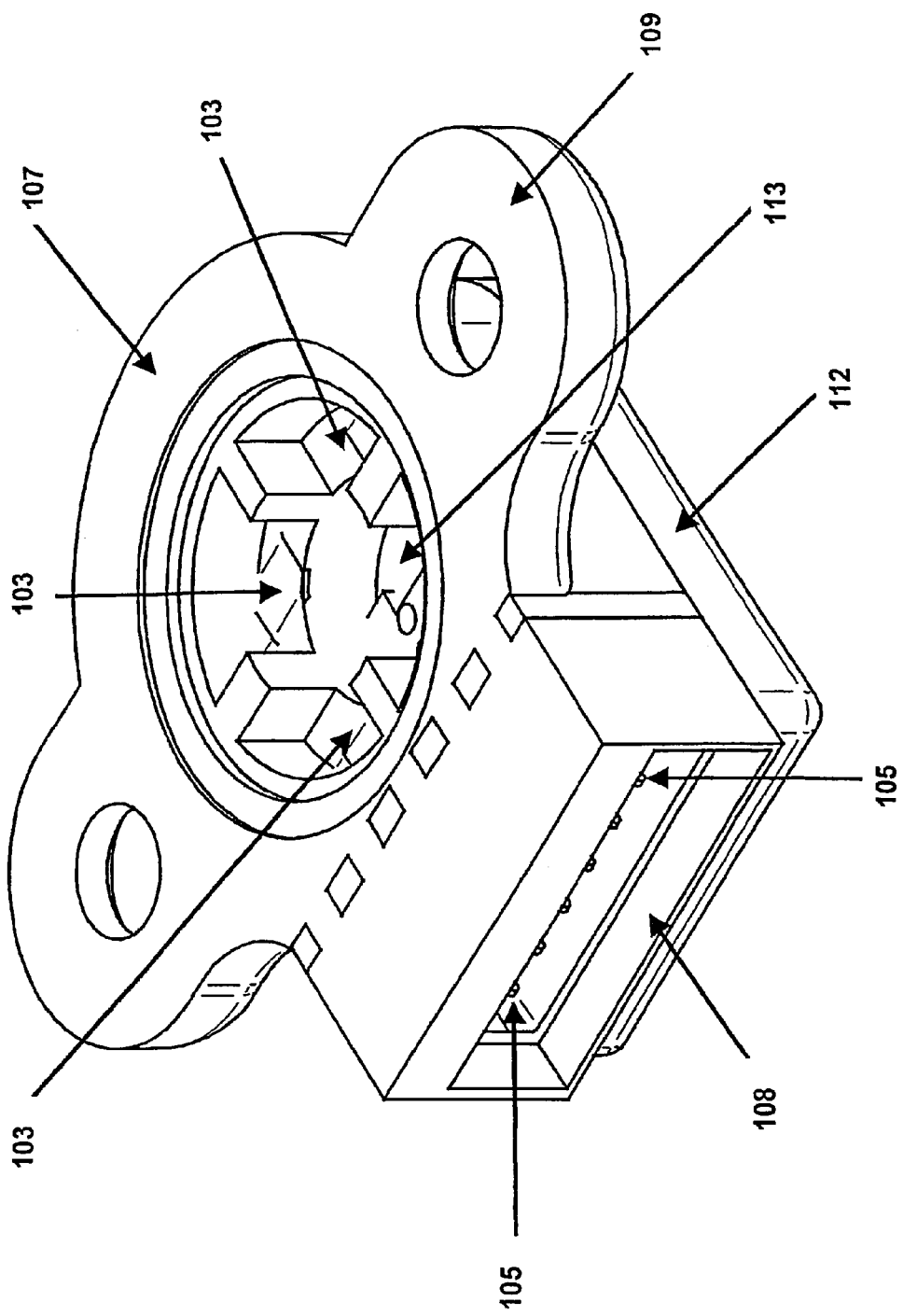
Figure 13:
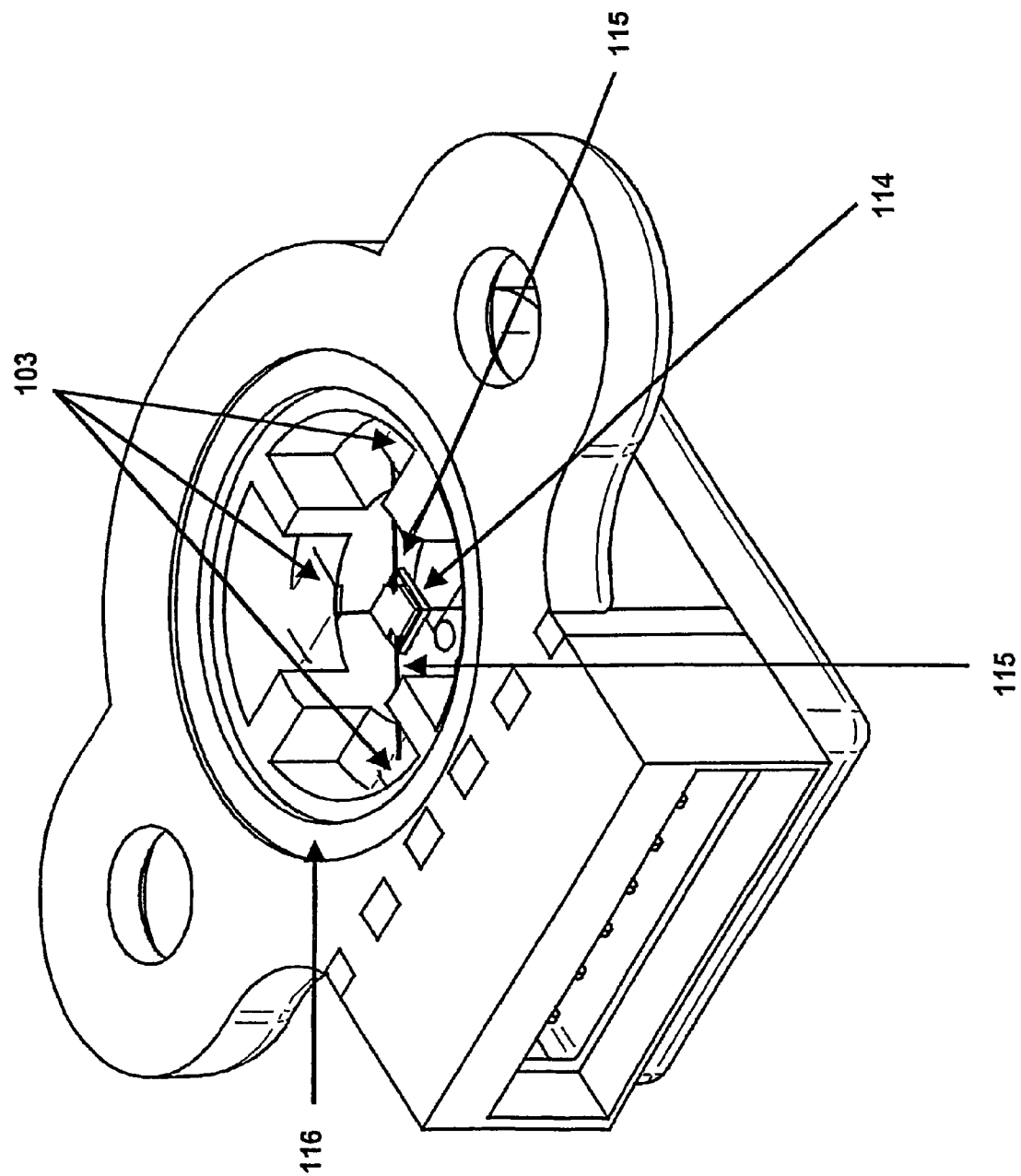

FIG. 5 comprises FIGS. 5a and 5b which show, respectively, a plan and a side view of a conducting lead frame before the housing has been moulded around it;

FIG. 6 is a circuit diagram of a detecting circuit attached to the device;

FIG. 7 is a perspective view of an example of a lead frame which may be employed in a gas sensing device in accordance with a second aspect of the invention;

FIG. 8 is a perspective view of the lead frame shown in FIG. 7 overmoulded with a first portion of a plastics housing;

FIG. 9 is a perspective view of the lead frame shown in FIG. 7 overmoulded by both an inner portion of the plastics housing and an outer portion of the plastics housing;

FIG. 10 is a perspective view of the assembly shown in FIG. 9 with an electronic component shown connected to the lead frame;

FIG. 11 is a perspective view of the completed gas sensor device;

FIG. 12 is an underneath perspective view of the overmoulded lead frame; and,

FIG. 13 is an underneath perspective view of the overmoulded lead frame with the gas sensing element in place.

The gas sensing device shown in FIGS. 1 to 4 comprises a plastics housing 1, made from a material such as PEI (polyetherimide), PPS (polyphenylsulphide) or PTFE for example, moulded around a metal lead frame 2, which is shown in more detail in FIG. 5. The housing includes a wall 10 which surrounds a cavity, at the base of which is a substantially square recess 12 which itself is surrounded by a raised, ridged shelf 11 which is substantially circular. In the floor of the recess 12 are two further recesses 13 containing glass wool 9 which acts as a shock absorber and insulator.

Figure 1:
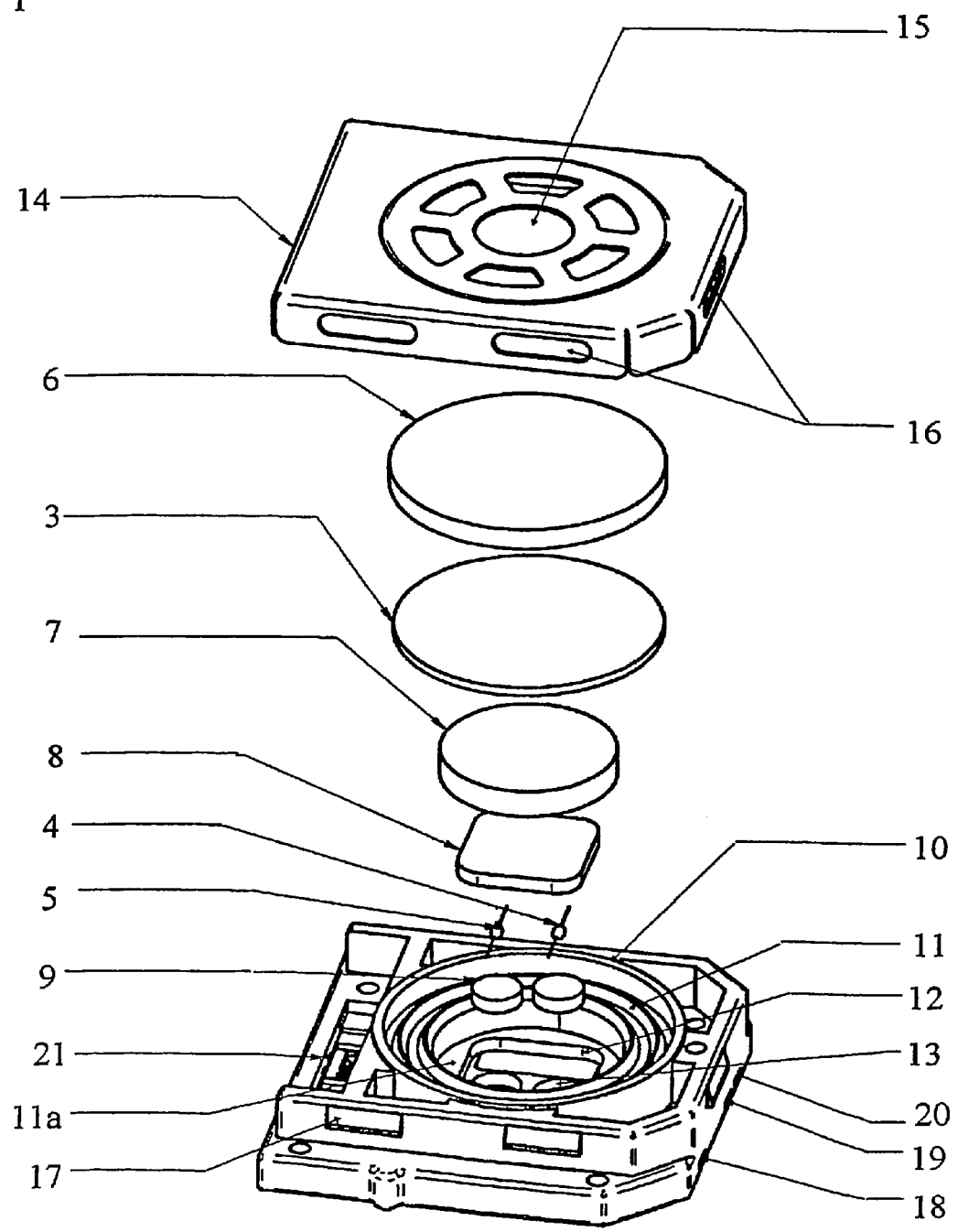
FIG. 1 shows an exploded view of a gas sensing device in accordance with a first aspect of the invention.

Mounted in the housing 1 are two conventional pellistor gas sensing elements: a detector 4 and a compensator 5. Each element comprises a metal filament encased by a porous bead, the detector element 4 including also a catalyst which may be chosen according to the gas which is to be detected. The elements 4 and 5 are connected to the lead frame 2 by means of conducting cement or welding, for example. The metal leads are encapsulated by the wall of the housing 10 and exit the housing body as tabs 22-24 as shown in FIGS. 2 and 3, although in other examples they may not extend through the apertures 18-20 as shown in FIG. 1.

A second layer of glass wool 8 is located above the gas sensitive elements 4 and 5, inside the recess 12. A hydrogen sulphide filter 7 rests on the housing floor 11a above the recess 12. The $H_2S$ filter 7 is typically fabricated using a paper or glass wool filter impregnated with lead acetate and as such it is desirable that it is inboard of the flame arrestor 3 to prevent users from coming into contact with it. An enclosure is created by the joining of the metal mesh flame arrestor 3 to the top of the shelf 11, which is sufficiently wide to ensure that the resulting joint is at least 1.25 mm wide. The mesh 3 allows the passage of gas into the cavity yet acts as a flame arrestor and thus renders the enclosure flameproof. A second, silica filter 6 is located on the outboard side of the flame arrestor 3 and comprises a glass fibre disc coated with 25% Si. Its purpose is to absorb chronic, irreversible pellistor catalyst poisons such as the silicone HMDS. The two filters 6 and 7 together remove contaminants from the gas flow into the device. It is also envisaged that plural filters such as 6 and 7 could be combined into a single, multi-purpose filter, although this is not shown in the drawings.

A metal bezel 14 clips onto the housing 1 in order to hold components such as filter 6 in place and to provide the device with protection. The bezel 14 is provided with a number of holes 16 which enable the bezel 14 to be fastened to the housing 1 by means of a corresponding number of barbs 17 on the housing exterior. The bezel 14 also incorporates one or more holes 15 through which gas may enter the device.

Figure 2A:
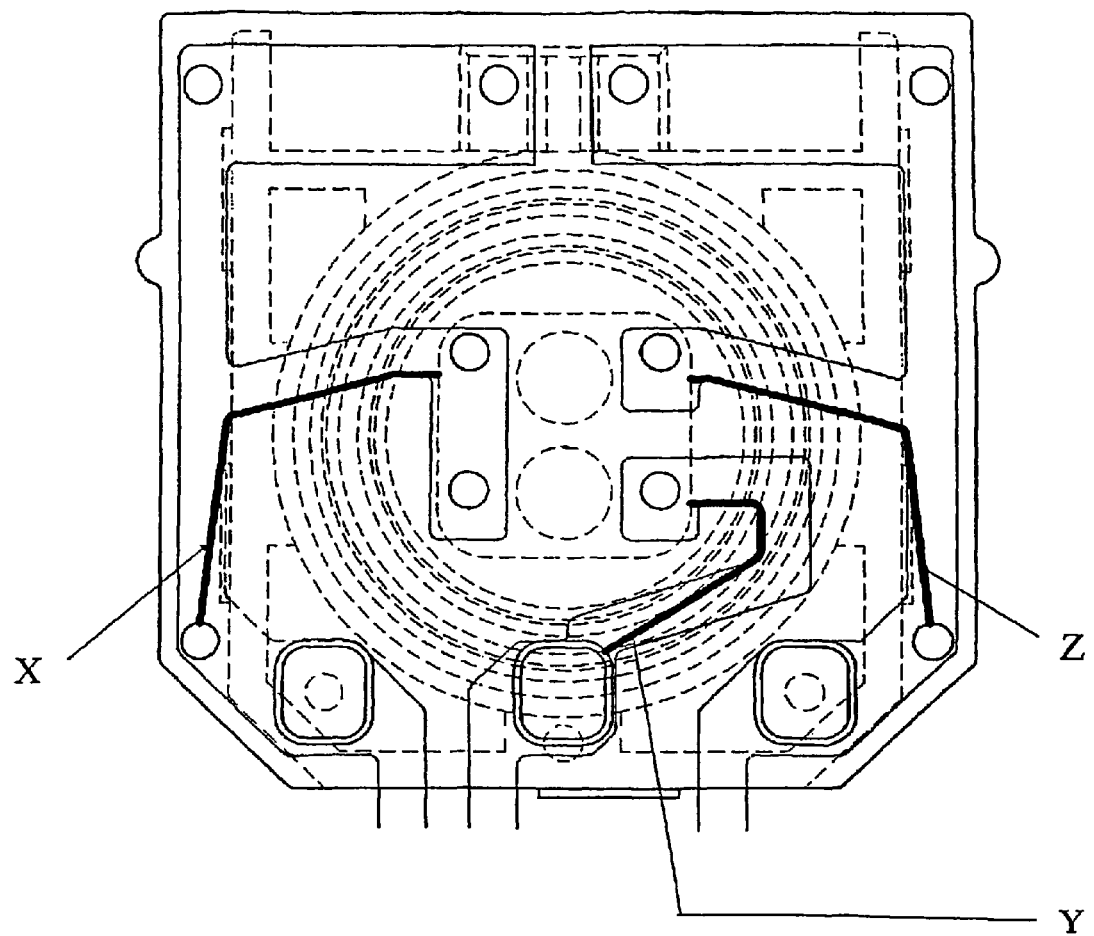
FIG. 2A is a schematic underneath plan showing projections of the uppermost features of the devices as dashed lines, the location of the lead frame in solid lines and shortest distances along the conducting path, though the wall of the housing in bold.

The features of the housing 1 are shown in plan view in FIG. 2. The dashed lines indicate the position of the lead frame 2. The gas sensitive elements 4 and 5 are connected to the lead frame 2 which emerges from the housing as leads 22-24, through apertures 18-20. At least 6 mm of each conducting lead is encapsulated by the wall of the housing 1. FIG. 2A illustrates the shortest path on each of the three conducting lines which pass through the housing to connect the gas sensitive elements inside the flameproof enclosure to the detecting circuit outside. It is clear that the path marked "Y" is the shortest path and it is this path therefore which requires most scrutiny by the certifying authorities. Generally path "Y" must be at least 6 mm long. The lead frame 2 also comprises a trimming resistor 21 which is connected between the leads 23 and 24 and is present to compensate for differences in performance of the two elements 4 and 5.

FIG. 3 shows that the same leads 22-24 may be also accessed from beneath the device, through apertures 25-27 respectively, which are formed in an integral, lateral extension of the housing 1. This may be useful, for example, when mounting the device onto a printed circuit board (PCB). Again, the lead frame 2 is represented inside the housing by dashed lines. The circles L, seen also in FIGS. 1 and 2 are a result of the use of lead frame locating pins during the moulding process.

Figure 4:
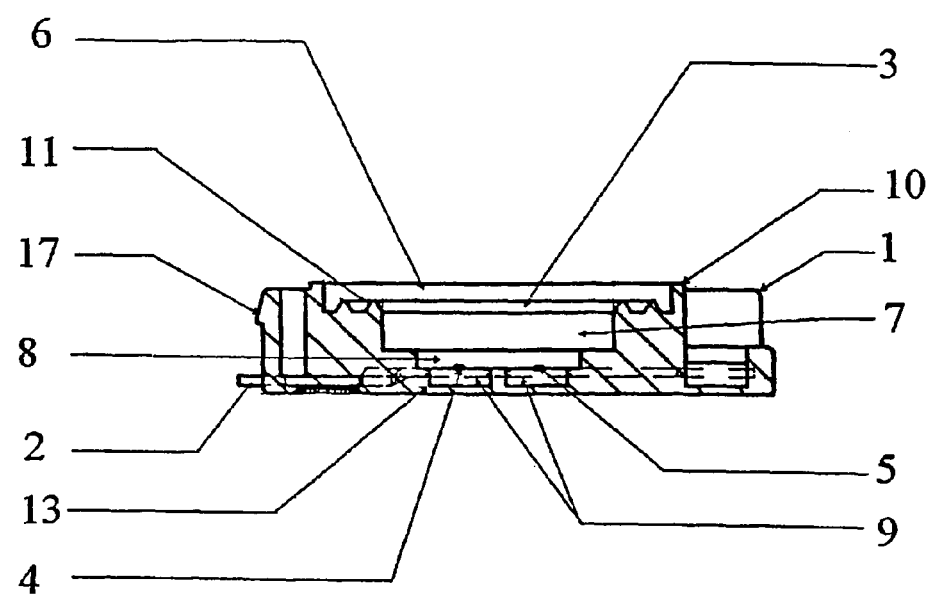
FIG. 4 is a section taken on the line A-A in FIG. 2, but illustrates a complete device with the exception of the metal bezel 14.

The arrangement of the layers can be seen most clearly in FIG. 4. The gas sensitive elements 4 and 5 are shown to be sandwiched between layers of glass wool 8 and 9 which provide protection from mechanical shock, electrical insulation and insulation from heat loss. In a typical arrangement, the depth of the recess 13 over which the element 4 or 5 is located is approximately 0.5 mm and its diameter 2 mm. The recess 12 above the gas sensitive elements is generally about 1 mm deep and 5 mm by 5 mm in area. The device has a total height of approximately 4 mm.

The all-metal lead frame 2 is shown in more detail in FIG. 5, prior to its encapsulation by the plastics housing 1. Once the housing 1 has been moulded around the lead frame 2, the metal is cut along line 34 to separate the conducting leads. This line need not coincide with the outer edge of the plastics housing and in particular conducting leads may be left protruding from the housing, as shown in FIGS. 2 and 3. It is envisaged that the lead frame is constructed from beryllium copper, with a hard acid gold plating layer, substantially 0.5 microns in thickness, over electroless nickel. However, any number of other variants could in principle satisfy the same requirements of good mechanical stability, resistance to degradation caused by aggressive operational environments and good electrical conductivity. It would also be possible to have a lead frame 2 in the form of a pre-moulded subassembly, in which the joining part 35 is an insulating material and may therefore remain attached, for example to assist in placing the device into an instrument. As shown in FIG. 5b, the lead frame 2 need not be flat. In the example shown, most of the interior portion of the lead frame 2 is raised slightly with respect to the exterior parts.

The detector element 4 is connected between points 28 and 29 on the lead frame 2, and the compensator element 5 between points 30 and 31 by means of conducting cement or welding, for example. The trimming resistor 21 joins points 32 and 33. Layers 8 and 9 of glass wool are packed above and below the elements 4 and 5 and a filter 7 is positioned on the housing floor, on top of the glass wool 8. The flame arrestor 3 is joined around its perimeter to the top of the shelf 11 of the housing 1 by means of a thermal bonding process such as heat staking. Filter 6 is then located on the outboard side of the flame arrestor, and held in place by the metal bezel 14, which is mechanically fastened to the housing by means of barbs 17 and holes 16. In use, gas passes though the bezel 14, the flame arrestor 3, both filters 6 and 7 and at least one layer of glass wool 8 to reach the detecting element 4.

FIG. 6 is a circuit diagram to illustrate a Wheatstone bridge circuit which incorporates the two elements 4 and 5. As described above, the elements are coupled to leads 22-24, with a trimming resistor 21 between leads 23 and 24. The lead 24 forms one output 36 of the circuit directly. Leads 22 and 23 are joined to resistors R1 and R2 at points 37 and 38 respectively. Resistors R1 and R2 are connected at point 39 to a variable resistor 40. Point 39 also provides the second output 41. DC power is supplied to the circuit at 42, and is used to heat the elements 4 and 5 to their working temperature of approximately 500° C. as well as to power the circuit. However, it should be noted that the sensors could also be operated in circuits other than the Wheatstone bridge described above.

An example of a gas sensing device in accordance with a second aspect of the invention will now be described with reference to FIGS. 7 to 13. The sensing device consists of a conductive lead frame 100, partially encapsulated by a plastics housing 106 and 107, a gas sensitive element connected to the conducting lead frame 100 and an electronic component 110 also connected to the conducting lead frame 100.

A conducting lead frame 100 is shown in FIG. 7. This component performs a number of functions. In particular, it provides physical support for the sensor, electrical connections to and from the sensor, electrical connections to and from any additional components which may be incorporated within the gas sensing device, interconnections between the sensor and the additional electronic components and the basic structure of the electrical connector used to interface the completed device to the remainder of the operating circuitry.

The lead frame 100 may be constructed from a range of conductive materials, typically metals such as copper or steel. Nickel-coated phosphor bronze is particularly well suited to the application. The lead frame 100 may be fabricated in a number of ways, for example by a photolithography and etching sequence, or by a series of stamping and bending processes (progressive forming). The detailed shape of the structure is dictated by not only the requirements of the sensor and additional component circuitry but also the eventual physical envelope of the completed assembly.

Four pad areas 103 are provided on the lead frame 100 to allow connection to the gas sensitive element itself. Tabs 104 are formed into an array to facilitate direct connection of integrated circuit or discreet electronic components. The lead frame 100 illustrated in the Figures accepts an 8-pin package, but larger or smaller numbers of connections may be envisaged. It will be noted that some of tabs 104 are commoned together; others are connected to one or more of the sensor pads. In one case, a direct link between the two tabs across the electronic component is shown. Several tabs 104 are formed as extensions of connector pins 105 which act as the basis of the external connector.

In this initial form, the lead frame is provided with sacrificial parts 101 and 102 which greatly assist in handling the components during subsequent fabrication processes but which may be removed at appropriate stages by cutting or snapping along lines A and B which are provided with weakening grooves for this purpose.

The sensor housing 106 and 107 is formed by means of injection moulding with the lead frame in situ. In other words, the lead frame is positioned inside the mould during the injection moulding process. The housing is fabricated from thermoplastic materials such as polyphenylene sulphide (PPS) or liquid crystal polymer (LCP), although a range of such materials is available. A two-stage moulding process is used in which either the same or different polymeric materials may be used in each stage. This selection is largely dictated by the particular properties demanded of the finished component. For example, when using heated sensors, it may be that the region immediately surrounding the gas sensing element is required to have very stable properties at high temperature. In contrast, the external casing may need to offer resistance against a number of contaminants. Suitable polymeric materials may be employed for each location. Clearly, the plastic must be an electrical insulator to prevent short circuiting the lead frame 100.

In a first moulding step, a thermoplastic material is injection moulded around the lead frame 100 in order to form an inner portion 106 of the sensor housing. It should be noted that this first in situ moulding step leaves pad areas 103, tabs 104 and the ends of connector pins 105 exposed. In its unsupported state, the lead frame is fragile and flexible since the component is intended to be fully encapsulated in the final device. Thicker and hence more expensive lead frames could be used to partially alleviate this problem, but in applications demanding very low cost, this is not an attractive option. Therefore, an important feature of this first moulding step is that it provides strength and so eases handling difficulties during the remaining processing stages. Once the initial moulding has been completed, the sacrificial extensions 101 and 102 may be removed, although in some circumstances, it may be helpful to leave either or both extensions in place until the subsequent moulding stage is complete.

FIG. 9 shows the gas sensing device after a second moulding step, in which the assembly as shown in FIG. 8 is overmoulded by a second volume of thermoplastic material. As discussed above, this material may be the same or different to that used in the first moulding step. The second thermoplastic material forms an outer portion 107 of the sensor housing. Like the inner portion 106, the outer portion 107 may be formed by in situ injection moulding. Two separate injection moulding tools may be used for the two stages, or a single tool allowing two or moulding shots might be used instead. As shown in FIG. 9, the outer portion 107 of the housing still leaves the pads 103 and tabs 104 exposed for component attachment. The second moulding step also forms the remainder of the connector shroud 108 and circular features 109 which are used to attach the completed device to the required apparatus.

It would be possible to overmould the lead frame 100 in a single step to produce the whole casing. However, this would not allow the material properties to be varied and could damage the lead frame. A limited amount of material can be moulded around such a flexible component as the lead frame 100 in a single step without causing significant distortion.

An electronic component 110, such as an EEPROM, is attached to the exposed lead frame at tabs 104 via component legs 111. These are preferably joined by soldering, and a re-flow process is advantageous in this context. However, conducting adhesive or other known methods can be used to secure and make electrical connection to component 110 (FIG. 10). In order to complete this part of the assembly, a pre-moulded top 112, shown in FIG. 11, is attached to housing 107 either by snap-fit methods, or glueing, welding or other bonding means. If required, top 112 can be made in a detachable form to allow component 110 to be changed, but this is unlikely to be cost effective in low-price applications. Top 112 could be overmoulded in an additional moulding step, although the effect of the high temperatures upon the electronic components 110 would need to be ascertained.

The underside of the assembly is shown in FIG. 12. The housing 107 encloses a volume 113 into which a gas sensitive element may be fitted. Pad areas 103 of the conducting lead frame 100 are exposed within the enclosure, allowing a gas sensitive element 114 to be inserted into the cavity and electrically connected via leads 115 using soldering or conducting adhesive, for example (FIG. 13). In the example shown, sensor 114 is a planar device employing a semiconducting material whose electrical properties vary in response to the composition of the surrounding gas atmosphere. Particularly, a p-type mixed metal oxide semiconducting material of the first, second and/or third order transition metal series may be selected, which is responsive to a change in concentration of carbon monoxide in the surrounding atmosphere and also to a change in the concentration of oxygen in the surrounding atmosphere. For example, the sensor 114 shown could comprise chromium titanium oxide, but other forms of sensor might be employed, such as those based on conducting polymers or ion selective FET structures.

After attachment of the sensor 114, the enclosure may be sealed if required by a mesh, sinter, cap, membrane or other means allowing ingress of gas to the enclosed volume. This may advantageously be mounted on lip 116 by a suitable method such as heat staking, welding or glueing, depending on the intended application. Filters may also be incorporated in-board or out-board of the seal, and retained by the seal or another closure component.

In this example, the electrical component 110 is shown as a memory chip which might contain a variety of information useful to the sensor operator, such as calibration data or data relating to the target gas species. It is envisaged that the connections provided by pins 105 would allow this data to be interrogated by the user and this is also quite feasible that rewriting of the data into user accessible regions of the memory could be undertaken, perhaps as a result of in-field calibrations. Additionally, or instead of a memory chip such as a EEPROM, the lead frame could readily support a range of other components such as analogue to digital converters, amplifiers or microprocessors.

The completed gas sensing device may be mounted to any desired surface by means of fixing points 109 (FIG. 9) with screws or nails for example. The device may be electrically connected to an external circuit via connection pins 10.5. The pins 105 are housed within a connector shroud 108 which may be designed to fit with a connection plug.

The invention claimed is:
1. A gas detector comprising:
   a metal connecting frame having a plurality of conductors extending between first and second ends, the plurality of conductors formed into connector pins on the first end with a first portion of the plurality of conductors on the second end formed into a plurality of pads and a second, different portion of the plurality of conductors on the second end formed into an array of tabs; and a housing having a first portion formed of a first type plastic, the first portion, at least in part, surrounds the frame with elongated portions of the frame extending through and encapsulated by portions of the first type of plastic with other portions of the frame accessible to provide contacts exterior to the first portion, and with the encapsulated portion of the frame forming a flame proof seal with the encapsulating first portion with the housing having a second outer plastic portion, the second portion is molded over and encloses the first portion and non-contact portions of the frame, and is formed of a different plastic material with the second outer portion forming a partially enclosed molded plastic sensing region that supports the plurality of pads for a gas sensor with the second portion defining a gas inflow port and with a side of the second portion opposite the partially enclosed molded plastic sensing region supporting the array of tabs as a basis for an external connection to which electronic components may be mounted on an exterior of the housing, wherein the second portion forms a shroud around the connector pins and wherein each of the plurality of conductors extend from the connector pins into the housing along a single plane, with the first portion of the plurality of conductors extending to respective pads on opposing sides of the partially enclosed molded plastic sensing region such that the flame proof seal is formed from at least a predetermined minimum length of each conductor of the first portion of conductors encapsulated in plastic and wherein at least one conductor of the first portion of conductors follows a U-shaped path within the plastic to provide the predetermined minimum length.

2. A gas detector as in claim 1 where the encapsulated portion of the frame is at least 6 mm long.

3. A gas detector as in claim 1 where the sensing region is closed by a flame arrestor that covers the inflow port.

4. A gas detector as in claim 3 where the flame arrestor comprises a metal mesh.

5. A gas detector as in claim 4 where the metal mesh is, in part, bonded to the second, outer, portion by plastic filling voids in the mesh adjacent thereto.

6. A gas detector as in claim 4 which includes a filter located in the sensing region between the gas sensor and the metal mesh.

7. A gas detector as in claim 1 wherein the second, outer, portion carries an electronic storage unit coupled to at least some of the contacts.

* * * * *